US009326719B2

(12) United States Patent
Akkin et al.

(10) Patent No.: US 9,326,719 B2
(45) Date of Patent: May 3, 2016

(54) MEASUREMENT OF NEURAL FUNCTIONALITY USING PHASE SENSITIVE OPTICAL COHERENCE REFLECTOMETRY

(71) Applicant: Board of Regents, The University of Texas System, Austin, TX (US)

(72) Inventors: Taner Akkin, Minneapolis, MN (US); Thomas E. Milner, Austin, TX (US); Digant P. Dave, Arlington, TX (US); H. Grady Rylander, III, Round Rock, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 153 days.

(21) Appl. No.: 13/720,563

(22) Filed: Dec. 19, 2012

(65) Prior Publication Data

US 2014/0171807 A1   Jun. 19, 2014

Related U.S. Application Data

(62) Division of application No. 12/717,735, filed on Mar. 4, 2010, now Pat. No. 8,352,022, which is a division of application No. 11/136,213, filed on May 24, 2005, now Pat. No. 7,711,416.

(60) Provisional application No. 60/573,785, filed on May 24, 2004.

(51) Int. Cl.
   *A61B 6/00*   (2006.01)
   *A61B 5/00*   (2006.01)
   (Continued)

(52) U.S. Cl.
   CPC ............... *A61B 5/40* (2013.01); *A61B 5/0066* (2013.01); *A61B 5/0075* (2013.01);
   (Continued)

(58) Field of Classification Search
   CPC ........ A61B 5/40; A61B 5/0075; A61B 5/0622; A61B 5/7282; A61B 5/7225; A61B 5/0066; A61B 5/0082; A61N 1/00
   USPC .......................................................... 600/476
   See application file for complete search history.

(56) References Cited

U.S. PATENT DOCUMENTS

| 4,653,917 A * | 3/1987 | Moeller et al. ................. 356/466 |
| 5,187,672 A | 2/1993 | Chance et al. ................. 364/550 |

(Continued)

OTHER PUBLICATIONS

Akkin et al., Interferometric Fiber-Based Optical Biosensor to Measure Ultra-Small Changes in Refractive Index, Proceedings of SPIE, vol. 4616, p. 9-12, 2002.*

(Continued)

*Primary Examiner* — Bo J Peng
(74) *Attorney, Agent, or Firm* — David G. Rosenbaum; J. Peter Paredes; Rosenbaum IP, P.C.

(57) ABSTRACT

Optical methods, devices, and systems for noninvasively detecting transient surface displacements in a neuron are disclosed. Methods, devices, and systems provided may employ a phase-sensitive optical low coherence reflectometer. In addition, surface displacements due to action potential propagation in neural tissues may be detected in some embodiments using back-reflected light. According to some embodiments, exogenous chemicals or reflect ion coatings are not required. Transient neural surface displacement of less then 1 nm in amplitude and 1 ms in duration may be detected and may be generally coincident with action potential arrival to the optical measurement site. The systems and methods may be used for noninvasive detection of various neuropathies such as retinal neuropathies. They may also be useful in detecting the effects of various pharmacological agents.

13 Claims, 4 Drawing Sheets

(51) Int. Cl.
A61N 1/00 (2006.01)
A61N 5/06 (2006.01)
A61N 1/36 (2006.01)

(52) U.S. Cl.
CPC ............ *A61B 5/0082* (2013.01); *A61B 5/4029* (2013.01); *A61B 5/7225* (2013.01); *A61N 1/00* (2013.01); *A61N 1/3605* (2013.01); *A61N 5/0622* (2013.01); *A61B 5/6821* (2013.01); *A61B 5/7282* (2013.01)

(56) References Cited

U.S. PATENT DOCUMENTS

| | | | |
|---|---|---|---|
| 5,792,051 A | | 8/1998 | Chance .......................... 600/310 |
| 5,991,697 A | * | 11/1999 | Nelson et al. .................... 702/49 |
| 6,015,969 A | * | 1/2000 | Nathel et al. .............. 250/227.27 |
| 2004/0179202 A1 | | 9/2004 | Sezginer ........................ 356/451 |

OTHER PUBLICATIONS

Akkin, T., et al., "Detection of neural activity using phase-sensitive optical low-coherence reflectometry" *Optics Express* 12(11): 2377-2386 (2004).

Akkin, T., et al., "Imaging tissue response to electrical and photothermal stimulation with nanometer sensitivity" *Lasers in Surgery and Medicine* 33: 219-225 (2003).

Akkin, T., "Biomedical application of a fiber based low-coherence interferometer for quantitative differential phase measurements" *Dissertation: The University of Texas at Austin* pp. 1-153 (2003).

Born, M., et al., "Principles of optics: Electromagnetic theory of propagation, interference and diffraction of light" *Cambridge University Press* pp. 837-840 (1999).

Bryant, S.H., et al., "Optical and mechanical concomitants of activity in carcinus nerve" *Journal of Cellular and Comparative Physiology* 46: 71-95 (1955).

Cohen, L.B., et al., "Changes in axon birefringence during the action potential" *Journal of Physiology* 211:495-515 (1970).

Cohen, L.B., et al., "Light scattering and birefringence changes during activity in the electric organ of *Electrophorus electricus*" *Journal of Physiology* 203: 489-509 (1969).

Cohen, L.B., "Changes in neuron structure during action potential propagation and synaptic transmission" *Physiological Reviews* 53(2): 373-418 (1973).

Dave, D., et al., "Phase-sensitive frequency-multiplexed optical low-coherence reflectometery" *Optics Communications* 193: 39-43 (2001).

Hill, D.K., et al., "Laser interferometer measurement of changes in crayfish axon diameter concurrent with action potential" *Science* 196: 426-428 (1977).

Hill, D.K., "The volume change resulting from stimulation of a giant nerve fiber" *Journal of Physiology* 3: 304-327 (1950).

Iwasa, K., et al., "mechanical changes in squid giant axons associated with production of action potentials" *Biochemical and Biophysical Research Communications* 95(3): 1328-1331 (1980).

Lazebnik, M., et al., "Functional optical coherence tomography for detecting neural activity through scattering changes" *Optical Letters* 28(14): 1218-1220 (2003).

Maheswari, R.U. et al., "Novel functioning imaging technique from brain surface with optical coherence tomography enabling visualization of depth resolved functional structure in vivo" *Journal of Neuroscience Methods* 124: 83-92 (2003).

Muralt, A., "The Optical Spike" *Phil. Trans. R. Soc. Lond. B.* 270: 411-423 (1975).

Rylander, C., et al., "Quantitative phase-contrast imaging of cells with phase-sensitive optical coherence microscopy" *Optics Letters* 29(13): 1509-1511 (2004).

Tasaki, I., et al., "Rapid mechanical and thermal changes in the garfish olfactory nerve associated with a propagated impulse" *Biophysical Journal* 55: 1033-1040 (1989).

Tasaki, I., et al., "Volume expansion of nonmyelinated nerve fibers during impulse conduction" *Biophysical Journal* 57: 633-635 (1990).

Tearney, G.J., "High-speed phase- and group-delay scanning with a grating-based phase control delay line" *Optics Letters* 22(23): 1811-1813 (1997).

Yao, X., et al., "Optical lever recording of displacements from activated lobster nerve bundles and *Nitella* internodes" *Applied Optics* 42(16): 2972-2978 (2003).

* cited by examiner

MEASUREMENT OF NEURAL FUNCTIONALITY USING PHASE SENSITIVE OPTICAL COHERENCE REFLECTOMETRY

CROSS REFERENCE TO RELATE APPLICATIONS

The present application is a divisional application of U.S. patent application Ser. No. 12/717,735, filed Mar. 4, 2010, which is a divisional of U.S. patent application Ser. No. 11/136,213, filed May 24, 2005, now U.S. Pat. No. 7,711,416, issued May 4, 2010, which claims priority to U.S. Provisional Patent Application Ser. No. 60/573,785, filed May 24, 2004, all incorporated by reference in their entirety herein.

GOVERNMENT SUPPORT

This invention was made with government support under Contract No. EY12877 awarded by the National Institutes of Health. The government has certain rights in the invention.

TECHNICAL FIELD OF THE DISCLOSURE

The present disclosure relates to non-invasive systems methods of measuring neural activity. More specifically, it relates to determination of neural activity through measurement of transient; surface displacement of a neuron.

BACKGROUND

Optical assessment of neural activity typically requires an invasive detection system. For example, axons may be coated with nanometer-diameter gold particles to assess neural activity by measuring sapid changes in axon diameter using a laser interferometer. Differences in reflected or back-reflected light from these particles may then be detected by the interferometer. Rapid mechanical changes may also be assessed using a piezoceramic bender attached to the axon and a stylus. Similarly, an optical lever may be configured such that one edge rests on an axon and an opposing edge rests on a fixed point (e.g., a knife edge). Swelling or shrinkage of the axon may be assessed by detecting changes in reflection of incident light. In addition, slow changes (on the order of a few seconds to a few minutes) in neural activity may be detected using optical coherence tomography, but this technique is insensitive to rapid changes (on the order of 20 milliseconds) and small changes (on the order of nanometers).

Due, at least in part, to their invasiveness, the above-described techniques are typically not useful in a clinical setting.

SUMMARY

Accordingly, in view of the importance of in vivo detection of neural activity, a demand exists for less invasive methods and devices for detecting neural activity during neural propagation.

Some embodiments of the present disclosure provide methods, devices, and/or systems for assessing (e.g., detecting, measuring, monitoring, and/or processing) activity of a neuron Subject neuron(s) may be assessed while resting or originating or propagating a neural signal. Activity may be assessed as displacement of one or more neural surfaces (e.g., cell surface) in some embodiments. For example, neural activity may be assessed through transient surface displacement such as shrinking or swelling. Embodiments of the disclosure may characterize functionality of nerves by assessing transient surface displacement associated with neural activation.

According to some embodiments, the disclosure provides methods, devices, and/or systems for assessing neural activity non-invasively. For example, neural activity may be assessed without contacting the subject cell(s) with a detection aid (e.g. a contrast agent or a reflection coating). Some embodiments of the disclosure use non-contact, sub-nanometer optical measurement of neural surface displacement associated with action potential propagation.

Embodiments of the disclosure provide a system for assessing activity of a neuron comprising an interferometer, an optical spectral analyzer, and optionally a processor. An interferometer may comprise, for example, light emission optics, light combining optics, light splitting optics, reference beam optics, sample path optics, recombiner optics, light detect ion optics, optical spectral analyzer, and optionally a processor. Reference beam optics may include a reflector and/or a phase modulator in some embodiments. A reflector may be configured with other components to form an optical delay line. Sample path optics may include birefringent wedges, a microscope objective, and/or a sample.

BRIEF DESCRIPTION OF THE DRAWINGS

Some specific example embodiments of the disclosure may be understood by referring, in part, to the following description and the accompanying drawings, wherein.

DETAILED DESCRIPTION

Figure 1:
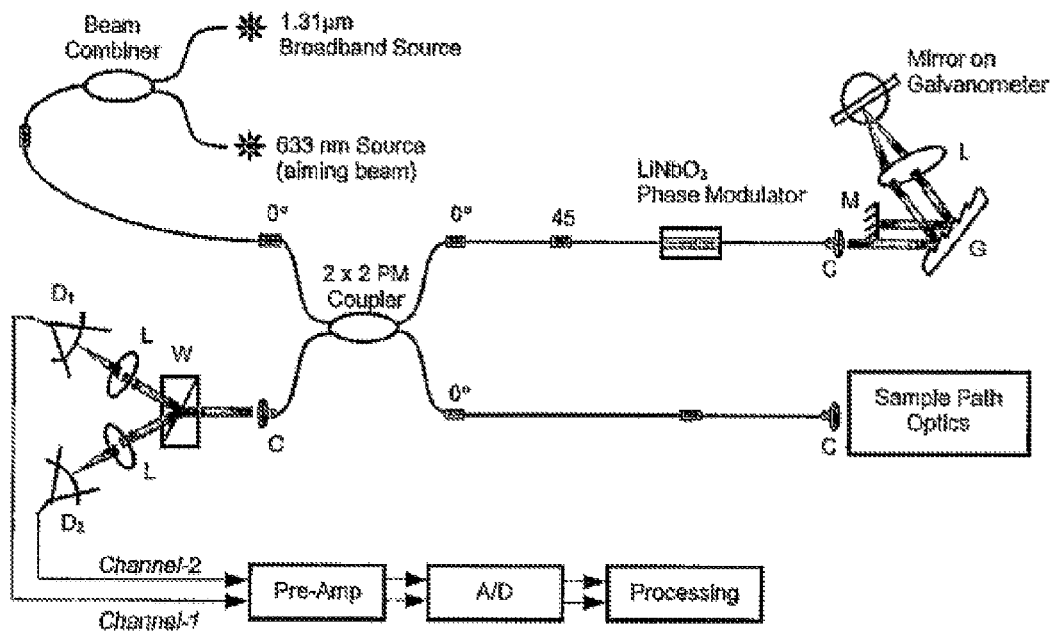
FIG. 1 illustrates an embodiment of a Phase Sensitive Optical Low Coherence Reflectometer (PS-OLCR), as may be used in embodiments of the present disclosure. The following abbreviations are used in the figures: A/D—analog to digital converter, C—collimator, D—photoreceiver, G—diffraction grating, L—lens, M—mirror, W—Wollaston prism.

According to some embodiments, methods, devices, and/or systems of the disclosure may be used to assess the condition of any neural cell. Neural cells may be assessed while in any state including, without limitation, any developmental state, any physiological state, any electrical state, any chemical state, and/or any pathological state. In each case, the state may be normal or abnormal, active or inactive. In some embodiments, methods, devices, and/or systems of the disclosure may be used to detect, assess, and/or diagnose a neural pathology. Neural pathologies that may be detected, assessed, and/or diagnosed include, without limitation, ailments, diseases, illnesses, infirmities, and/or maladies (whether of sudden or gradual development). Conditions and/or pathologies may be detected, assessed, and/or diagnosed upon their first occurrence or at any time thereafter. For example, methods, devices, and/or systems of the disclosure may be used for early diagnosis of glaucoma, a leading cause of blindness. According to other embodiments, neural diseases outside of the eye (e.g., multiple sclerosis and Alzheimer's) may be detected, assessed, and/or diagnosed.

Methods, devices, and/or systems of the disclosure may be used to assess any neural cell, tissue, and/or organ including, without limitation, brain, spinal cord, and peripheral nerves. For example, in an embodiment, methods, devices, and/or systems of the disclosure may be used to assess functionality of nerve fibers on the anterior surface of the retina.

In other embodiments of the disclosure, methods and devices of the disclosure may be used for non-invasively assessing neural activity in the presence and/or absence of one or more test compounds (e.g., small organic molecules, neurotransmitters, pharmacologic agents, and others). Thus, one of ordinary skill in the art would recognize that a wide variety of assay combinations are possible. For example, activity of one or more neurons may be assessed, individually or collectively, in the presence of one or more test compound concentrations, and/or in the presence of different test compounds. Similar assessments may be performed in which a test compound is replaced by or complemented with a test stimulus (e.g., electrical, mechanical, gravitational, hydrostatic pressure, and others).

Techniques to non-invasively assess neural functionality in vivo are rare or non-existent. Although fluorescent techniques may detect action potential propagation using in vitro neuron preparations, administration of pharmacologic contrast agents may be required. Toxicity of the pharmacologic contrast agents precludes any potential clinical application of this or similar approach. Accordingly, some embodiments of the present disclosure in which such agents are non-essential may provide safer and/or less toxic means of neural detection.

While exogenous chemicals and/or reflection coatings optionally may be used in some embodiments, they are not required in most embodiments. The measured optical signal may be coincident with action potential arrival to the optical measurement site. Accordingly, PS-OLCR may be a valuable tool for fundamental nerve studies and noninvasive detection of various neuropathies.

In some embodiments, the disclosure provides methods of diagnosing a neuropathy comprising (a) assessing the transient surface displacement of a test neuron using a phase-sensitive optical low coherence reflectometer to obtain at least one surface displacement assessment, (b) comparing the at least one test neuron surface displacement assessment with control surface displacement assessments to produce a test neuron activity differential, and (c) processing the test neuron activity differential to detect inappropriate neural activity in the test neuron, wherein the inappropriate neural activity is indicative of a neuropathy. A test neuron activity differential may be a simple difference in the surface displacement at a specific time (e.g., 2 ms after a stimulus). Alternatively, it may be a difference between the surface displacement curve over a period of time. One of ordinary skill in the art will recognize that other mathematical operations may be performed to calculate a differential. The artisan of ordinary skill will also recognize that the operation applied to obtain the differential may vary according to the specific neuropathy being assessed. Likewise, the relationship between the differential and inappropriate neural activity will vary with the neuropathy, but may be readily determined empirically, for example, by comparing known healthy neurons with known diseased neurons at various levels of severity.

Also, although some optical techniques may reveal the structural integrity of the retinal nerve fiber layer, these techniques typically do not assess neural functionality. Some embodiments of the present disclosure may allow measurement of neural functionality in response to a multiplicity of user-selected (e.g., neurologist-specified) stimulation sequences.

According to embodiments of the disclosure, assessment of neural activity may be achieved by noninvasive optical assessment of neural surface displacement. Embodiments of the disclosure may characterize functionality of nerves by measurement of surface displacement associated with neural activation. Systems, devices, and methods of the present disclosure may use a fiber-optic phase-sensitive optical Low coherence reflectometer (PS-OLCR) and may be operable to detect a variety of neurological slates. According to some embodiments, methods, systems, and/or devices of the disclosure may use a PS-OLCR system capable of measuring ultra-small changes in optical path length using backreflected light from a neurological sample. In addition, double passage of light through the sample may be used in some embodiments to increase the detected phase delays by a factor of two.

The fiber-optic PS-OLCR system used in some embodiments of the present disclosure may be configured to incorporate a fiber probe for endoscopic and microfluidic biosensing applications. In addition, according to some embodiments, systems may be compact, portable and/or easy to align.

Embodiments of the present disclosure may include a depth-resolved interferometric technique useful to measure transient surface displacement (swelling or shrinkage) as a direct indication of neural activity, i.e., action potential propagation. An optical system may include a PS-OLCR, a fiber-based differential phase interferometer capable of measuring ultra-small (0.1 nm) changes in optical path length with microsecond (0.1 microseconds) or shorter temporal resolution. Sub-wavelength changes in optical path length in the nerve as a result of stimulation may be measured by extracting the phase difference between interferometric fringes measured by the PS-OLCR system in two channels corresponding to orthogonal polarization modes. Environmental phase noise in PS-OLCR systems may be eliminated by common mode detection. Comparing with single channel results, certain systems of the present disclosure improve the phase sensitivity by approximately 3-orders of magnitude (~60 dB). In one instrument that may be used in the present disclosure, phase sensitivity is one milliradian, which approximately corresponds to optical path length change of 1 angstrom when the source wavelength is centered at 1.31 μm.

PS-OLCR may be well suited to noninvasively detect and/or quantify transient surface displacement in nerves associated with the action potential propagation. Experiments performed in accordance with the present disclosure using nerve bundles dissected from crayfish leg without introducing any chemicals or reflection coatings reveal that measured transient surface displacement was less than 1 nm in amplitude, 1 ms in duration and occurred simultaneously with the action potential arrival to the optical measurement site.

According to some embodiments of the disclosure, a single excitation/response measurement may be sufficient to measure action potential propagation. Some embodiments provide methods of boosting signal-to-noise ratio. For example, perturbations of the PS-OLCR phase information may be minimized including, without limitation, dispersion, existence of ghostlines, modulation and signal processing schemes, and factors that induce refractive index changes of polarization maintaining fiber (e.g., thermal drift, air currents and vibration).

In some embodiments, dispersion may be overcome by careful design of the optical-delay-line. According to others, effects of ghostlines may be eliminated by design of the PS-OLCR system using proper fiber lengths. The fiber system excluding the sample path may be placed in an insulating enclosure to prevent environmental perturbations.

The PS-OLCR devices and systems may be used in some embodiments to detect, transient changes in optical pathlength and birefringence in tissues in response to a variety of stimuli. Phase and intensity information map be used to evaluate structural properties in a tissue in response to a given excitation. The techniques may be used in situ to study the propagation of action potentials anywhere in the nervous system (e.g., central and peripheral).

Embodiments of the disclosure provide a system for assessing activity of a neuron comprising an interferometer, an optical spectral analyzer, and optionally a neural stimulator and/or a processor. A neural stimulator may stimulate neural activity electrically, chemically, optically, physically, or otherwise. Neurons may be exposed to combinations of electrical, chemical, optical, and/or other stimuli by a single neural stimulator or by separate stimulators. As such, the neural stimulator may be selected from the group consisting of an optical stimulator, an electrical stimulator, a chemical stimulator, and combinations thereof. An interferometer may comprise, for example, light emission optics (e.g., broadband source, aiming beam), light combining optics (e.g., light combiner), light splitting optics, reference beam optics, sample path optics, recombiner optics, light detection optics, optical spectral analyzer, and optionally a processor. Reference beam optics may include a reflector and/or a phase modulator in some embodiments. A reflector may be configured with other components to form an optical delay line. Sample path optics may include birefringent wedges, a microscope objective, and/or a sample.

Figure 2:
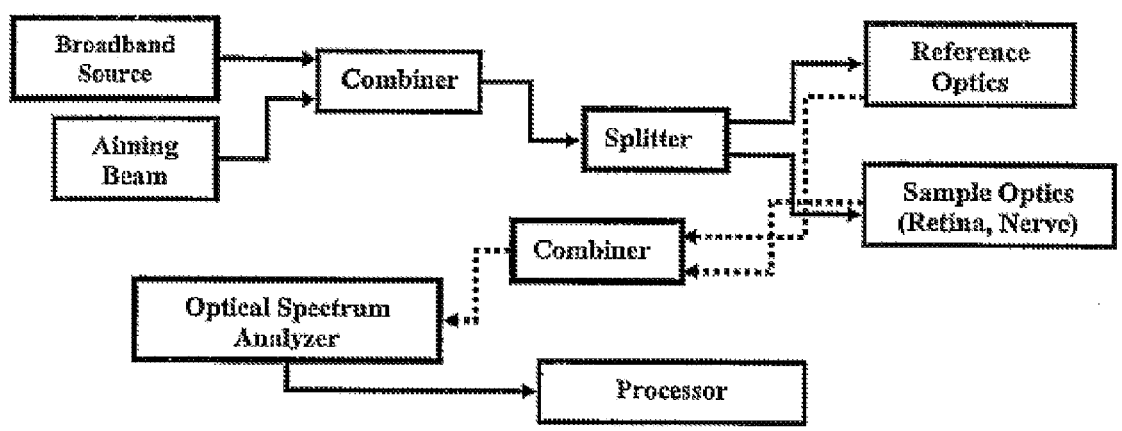
FIG. 2 illustrates an embodiment of PS-OLCR as may be used in embodiments of the present disclosure.

In the embodiment shown in FIGS. 1 and 2, an interferometer may comprise a beam combiner optically connected to a 1.31 μm broadband source and optically connected to a 633 nm source (aiming band). A beam combiner may be optically connected to a separator. As shown in FIG. 1, the separator may be 2×2 PM coupler, which, in the illustrated embodiment, serves as both the separator and recombiner. A reference path may be optically connected to the separator and comprise a 45° splice, a LiNbO$_3$ phase modulator, and a rapid scanning delay line. As shown, a rapid scanning optical delay line may comprise a collimator (C), a diffraction grating (G), a lens (L), mirror (M,) and a mirror on a galvanometer. The sample path may comprise any suitable optics for illuminating a sample. The sample path and the reference path may each be optically connected to a recombiner. As noted, the separator shown in FIG. 1 also serves as the recombiner. Alternatively, the recombiner may be distinct from the separator as shown in FIG. 2. The recombiner may be optically connected to a spectral domain detector (FIG. 1) or an optical spectrum analyzer (FIG. 2). An optical spectrum analyzer may detect backscattered radiation received by the interferometer to analyze modulated interference spectral densities produced by the interferometer.

A common optical arrangement to measure relative light intensity change (ΔI/I) associated with a transient retardation change (ΔR); retardation (R) is the product of birefringence (Δn) and nerve thickness (d). The arrangement consists of two crossed polarizers (polarizer and analyzer) at 90° orientation, while the nerve under study is placed between these components typically at 45° to the axes, which yields maxim intensity change. Measured intensity change during action potential propagation is due to a transient retardation change, ΔR=½R(ΔI/I), where R is the retardation due to the resting birefringence and I is the resting intensity of light. If nerve thickness (d) is constant, measured retardation change (ΔR) may be directly attributed to birefringence (Δn) change.

Some embodiments of the present disclosure may use PS-OLCR to measure retardation charge (ΔR) in reflection mode. For example, calcite birefringent wedges may be removed from the PS-OLCR sample path because interference fringes for both polarization channels may be recorded from a common interface underneath the nerve. The long axis of a nerve may be placed parallel to a PS-OLCR polarization channel. Although 10-20 pm resolution was achieved by averaging 1000 responses using methods and devices according to some embodiments of the present disclosure, no retardation change (ΔR) was detected in crayfish and squid nerves. Retardation changes using other techniques are 0.2 pm for a squid axon, 10 pm for a crab leg nerve, 60 pm for an electric organ of Electrophorus Electricus, and 41 pm for a pike olfactory nerve. In some embodiments, nerves containing multiple axons may be used in combination with increased number of averages to increase the effective retardation, thereby enabling detection of ΔR.

If refractive indices in two orthogonal. Directions change equally during neural activity, birefringence (Δn=n2−n1) may not change even though optical path length through the nerve might vary considerably. Transient change in optical path length during neural activity may be detected using PS-OLCR. Optical path length change using reflections from the air-glass interface of a cover glass (reference channel) and a saline-reflecting surface interface underlying the nerve (probing channel) have been recorded using embodiments of the present disclosure. At 10-20 pm resolution, no transient change in optical path length during neural activity was detected.

Birefringence may arise from either anisotropic molecules or an ordered arrangement of isotropic material with micro- or macro-scopic dimensions (form birefringence). If surface displacement contributes to retardation change (ΔR), the relative contribution ΔR from thickness change and reorientation of membrane molecules may require better quantification. Neural surface displacement in response to rapid repetitive stimuli that is as large as 100 nm may be useful to investigate changes in form-birefringence. Because repetitive stimulation may not increase retardation change (ΔR) due to reorientation of membrane molecules, effect of thickness change on ΔR may be investigated. In some embodiments, application of a PS-OLCR method, device, and/or system of the present disclosure may yield an early functional diagnosis of a neural disease. For example, methods, devices, and/or systems of the disclosure may be used in a clinical environment to characterize functionality of the nerve fibers on the anterior surface of the retina. They may also be used for early diagnosis of glaucoma, one of the leading causes of blindness.

According to some embodiments, the invention provides methods, devices, and/or systems for detecting transient surface displacement of optical neurons. For example, a PS-OLCR may be configured to include sample optics capable of direct light toward one or more neurons at the back of an eye, including, without limitation, human, primate, and other mammalian eyes. In embodiments in which a neural stimulator is present, it may be configured to induce neural activity in at least one ocular neuron. Reflectometers, interferometers, and neural stimulators of the disclosure may be configured to make little or no physical contact; with the eye. Whether or not contact is made, assessment of neural surface displacement may be made in association with another procedure, including, without limitation, cataract surgery, Lasik vision correction surgery, and/or intraocular device (e.g., lens) implantation surgery.

Applications outside of the eye, for example in the detection of other neural diseases such as multiple sclerosis and Alzheimer's may be achieved using still other embodiments of the disclosure. More broadly, methods, devices, and/or systems of some embodiments may be used to assess the functionality of all nervous tissue including the brain, spinal cord, and peripheral nerves.

Moreover, the certain systems and methods of the present disclosure may be useful for non-invasive physiologic monitoring in response to the application of pharmacologic agents. By measuring retinal neural functionality in response to administration of a pharmacological agent, systems of some embodiments may be useful to monitor various physiological states.

Because the applied excitation to elicit a neural response may take a variety of energetic forms (e.g., electrical, optical, acoustic) and time sequences, a broad horizon of potential diagnostic biomedical applications may be possible using various embodiments of the disclosure. For example, the system may be useful for detecting vulnerable plaques in coronary heart disease using as stimulation a photo-acoustic generated surface acoustic wave.

However, according to some non-limiting embodiments, methods, device, and/or systems may be used where optical access to a neural bed is available. The most optically accessible neural bed in humans is the retinal nerve fiber layer. In a variety of cranial surgical procedures optical access to neural beds in the brain may be obtained.

D. K. Hill suggested two mechanisms to explain initial neuron shrinkage observed with repetitive stimulation (D. K. Hill, "The volume change resulting from stimulation of a giant nerve fibre," J. Physiol. 111, 304-327 (1950)). Although results obtained using embodiments of the present disclosure are likely not due to such a cumulative effect, mechanisms discussed by Hill may be relevant to the present disclosure. First, Hill pointed out that potassium remains hydrated with water, which accompanies the ion through the membrane, whereas the sodium ion is not hydrated. Differences in hydration may shrink the nerve at the beginning of repetitive excitation and subsequent rate of swelling depends on membrane permeability to water. The observed shrinkage (0.5-1.5 nm) appears larger than that expected by this mechanism (D. K. Hill, "The volume change resulting from stimulation of a giant nerve fibre," J. Physiol. 3.11, 304-327 (1950)). In Hill's second explanation, the nerve swells because sodium and chloride enter the fiber due to a sudden increase in sodium permeability. If the interior of the nerve fiber is initially under hydrostatic pressure, the nerve fiber will shrink, which may cause a rapid extrusion of potassium and chloride ions in the active state. Therefore, the net ionic exchange may be inwards at the beginning of stimulation. In experiments using embodiments of the present disclosure, tying the nerve ends with sutures aids in positioning the nerve in the groove and prevents leakage of axoplasm, but may increase hydrostatic pressure in the axons.

Swelling observed in the squid giant axon was suggested to be more than two orders of magnitude greater than the value expected from $Na^+/K^+$ ion exchange during excitation (I. Tasaki, K. Kusano, and P. M. Byrne, "Rapid mechanical and thermal changes in the garfish olfactory nerve associated with a propagated impulse," Biophysical J. 55, 1033-1040 (1989)). results of a related study suggest that mechanical and electrical changes in the excited nerve fiber arise from replacement of divalent cations ($Ca^{2+}$) bound to multianionic sites of the membrane macromolecules with univalent cations ($Na^+$ and Kc) (I. Tasaki, and I. M. Byrne, "Volume expansion of non-myelinated nerve fibers during impulse condition," Biophysical J. 57, 633-635 (1990)). Such a cation exchange process may convert compact layers in and near the membrane into swollen, low-density structures, give a repulsive electrostatic force between fibrous macromolecular elements near the membrane and contribute to lateral expansion of the nerve fiber (I. Tasaki, and P, M. Byrne, "Volume expansion of non-myelinated nerve fibers during impulse conduction," Biophysical J. 57, 633-635 (1990)).

EXAMPLES

The following examples are provided to further explain specific examples of the invention. They are not intended to represent all aspect of the invention in its entirety. Variations will be apparent to one skilled in the art.

Example 1

General Methods and Equipment

A fiber-based dual channel PS-OLCR is illustrated in FIG. 1. The system is constructed with polarization maintaining (PM) Fujikura Panda fiber, whose polarization channels correspond to PS-OLCR channels. Fiber segments were spliced with a commercial system (Vytran FS 2000) that allows precise alignment of fiber cores and stress taxes. Small rectangles in FIG. 1 represent fiber splices and the values above show the splice angle in degrees between corresponding axes (slow and fast) of the two PM fiber segments.

A single mode, partially polarized light emitted by an optical semiconductor amplifier [$\lambda o=1.31$ μm and $\Delta\lambda$ (FWHM)≈60 nm] was combined with a 633 nm source (aiming beam) and delivered to the system, which provided approximately 15 μm axial resolution in tissue. The input PM fiber segment created two decorrelated linearly polarized modes that propagated along the birefringent axes of the fiber. Because an off-the-shelf 2×2 PM coupler is supplied with 1 meter fiber leads, length of input, reference and sample paths of the coupler were extended by splicing additional segments of PM fiber with axes at the same orientation (0° splice).

The lithium niobate ($LiNbO_3$) electro-optic waveguide phase modulator allowed light propagation of one linearly polarized state. The 45° splice in the reference path ensured that equal projections of the fast and slow polarization channels of input light were coupled into the modulation axis of the $LiNbO_3$ modulator. The modulator was driven with a ramp waveform with voltage amplitude ($V_\pi$) that gives sinusoidal fringe signals at a single carrier frequency. The rapid scanning optical delay line (G. J. Tearney, B. E. Bouma, and G. Fujimoto, "High-speed phase- and group-delay scanning with a grating-based phase control delay line," Opt. Lett. 22, 1811-1813 (1997)) shown in the reference path was configured to compensate material and waveguide dispersion introduced by the $LiNbO_3$ phase modulator. By adjusting the grating-lens separation in the rapid scanning optical delay line, width of the coherence function may be reduced to its minimum value. The 90° splice in the sample path and appropriate selection of segment-length allow centering coherence functions for each mode at the same position.

Longitudinally displaced orthogonal polarization channels FIG. 2 allowed measurement of optical path length change between two longitudinal points. Interference of light back reflected from reference and sample paths was formed in the 2×2 PM coupler. The Wollaston prism in the detection path separated the two fiber polarization channels for signal detection. Output of each photo-receiver was first amplified and band-pass filtered in the analog domain and then digitized by a 12 bit analog-to-digital converter. Digitized signals were was stored in computer memory for signal processing.

Forward and reverse band-pass filtering provided zero phase distortion and was used to de-noise the interferometric fringe data in the digital domain. Fringe phase in each channel was calculated by computing the angle between the signal and its Hilbert transform. The extracted phase data were unwrapped to remove phase jumps. Computing the differential phase ($\Delta\phi$) removed common mode environmental noise. Path length change due to surface displacement ($\Delta p$) was calculated from the differential phase ($\Delta\phi$) and the center wavelength of the source ($\lambda o$) using the equation: $\Delta p = (\lambda o / 4\Pi)\Delta\phi$. Signal to noise ratio and differential phase ($\Delta\phi$) sensitivity of the PS-OLCR system were limited by isolation of polarization channels in the PM fiber and associated cross-coupling between modes. Because signal to noise ratio was limited by cross-coupling between modes, the PS-OLCR system was not shot-noise limited. Additional details of the PS-OLCR instrument and biomedical applications have been reported (T. Akkin, "Biomedical applications of a fiber based low-coherence reflectometry" Opt. Comm. 193, 39-43 (2001); T. Akkin, D. P. Dave, J. Youn, S. A. Telenkov, H. G. Rylander 111, and T. E. Milner, "Imaging tissue response to electrical and photothermal stimulation with nanometer sensitivity," Lasers in Surg. Med. 33, 219-225 (2003), all incorporated by reference herein).

Example 2

Nerve Preparation

Structure and dissection of nerve is important for successful experiments. In some cases the optical signal did not yield surface displacement, although the action potential was recorded electrically. For example, although 0.5 nm swelling of squid giant axon was measured previously (K. Iwasa, and I. Tasaki, "Mechanical changes in squid giant axons associated with production of action potentials," Biochem. Biophysic. Res. Comm. 95, 1328-1331 (1980)), experiments on squid nerve (Lolliguncula brevis) using embodiments of the present invention were inconclusive. Histology sections indicate that squid nerves used in experiments with embodiments of the present invention consisted of a giant axon (150-200 µm), axons from the fin nerve and a thick connective tissue (perineurium) surrounding axon bundles. The connective tissue was believed to dampen or completely diminish the optical signal. Therefore, nerve specimen preparation requires adequate control. Accordingly, in some embodiments of the present invention, PS-OLCR may be incorporated with a microscope to assist in dissecting and targeting a region of the nerve or targeting a single axon.

Example 3

Results Using Crayfish Nerves

Crayfish were obtained locally and nerve bundles were dissected from front: walking legs using a surgical microscope. An extracellular solution of 205 mM NaCl, 5.3 mM KCl, 13.5 mM $CaCl_2.2H_2O$, and 2.45 mM $MgCl_2.6H_2O$ with pH adjusted to 7.4 was used to bathe the nerve during and after dissection. Before transecting the nerve, ends were tied with sutures to prevent leakage of axoplasm and assist with positioning. A chamber was constructed of plexiglass and attached to a three dimensional micropositioner for easy alignment in the PS-OLCR setup. The chamber shown in FIG. 2 consists of several pools and a groove, in which the nerve was positioned. The groove was approximately 20 mm long and 1 mm wide. To stimulate and record action potentials electrically, platinum stimulation and recording electrodes were placed into the pools and fixed with epoxy. A thin (200 µm) cover glass was glued on top of the groove between the two recording electrodes. Light reflecting from the coves glass-saline interface provided an optical reference signal.

After placing the nerve in the groove, pools filled with saline were electrically isolated with petroleum jelly. Between stimulation and recording sites, the electrical isolation pool was filled with petroleum jelly to reduce stimulation artifact in action potential recordings. A glass window (not shown) was positioned on top of the stimulation site for electrical isolation. An isolated current stimulator (Tektronix 8-timulus Isolator, Model 2620) was used to generate and apply 50 µs duration adjustable electric current (0-30 mA) stimulation pulses to the nerve. A differential amplifier (A-M System Microelectrode AC Amplifier, Model 1800) connected to the recording electrodes measured the action potential, which was recorded by a digital oscilloscope (Tektronix, Model TDS 640A). Tine interval between successive stimulation pulses was 1.028 s (0.973 Hz). Timing signals generated by a digital delay generator (Stanford Research Systems, Model DG535) synchronized stimulation pulses with data acquisition.

The probe beam in the PS-OLCR sample path (FIG. 2) was focused on the nerve using a 20× microscope objective to a diameter of 4 µm. First, saline-nerve (probe channel) and glass-saline (reference channel) interfaces were detected in PS-OLCR depth scans. Next, calcite birefringent wedges were positioned so optical path length of light reflected from both interfaces matched the reference path delay. With the reference delay line fixed, the $LiNbO_3$ phase modulator in PS-OLCR reference path gave sinusoidal fringes at 50 kHz. The detected fringe data was first band-pass filtered (3 kHz-100 kHz), then sampled at 5 M samples/s using a 12-bit data acquisition board (GaGe, CompuScope 12100). The data was stored in computer memory and transient surface displacement due to action potential propagation was calculated from the extracted phase difference between the sinusoidal fringes corresponding to reflection from the saline-nerve and glass-saline channels using commercial software.

Figure 3:
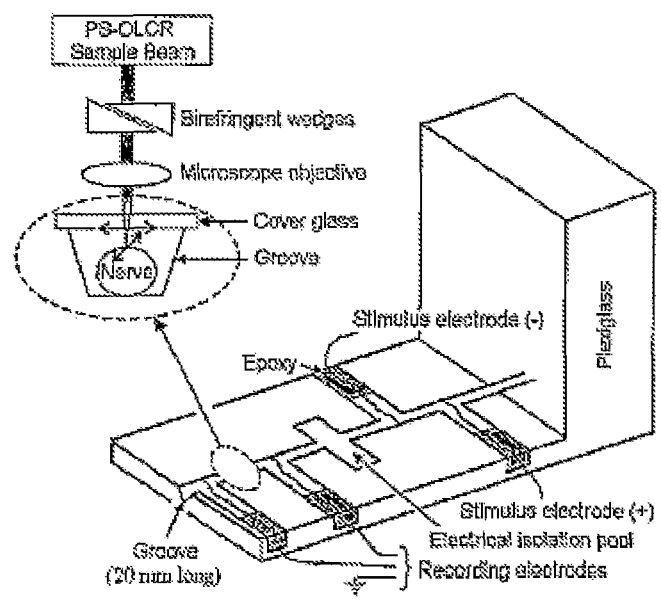
FIG. 3 illustrates a nerve chamber, according to certain embodiments of the present; disclosure. Double-sided arrows indicate the orthogonal polarization channels of PS-OLCR

Results indicated electrical action potentials associated with neural activity were correlated with optical path length changes corresponding to transient surface displacement of the nerve. Electrical and optical signals had 5 kHz bandwidth and were averaged to increase signal to noise ratio. FIG. 3 shows the average of 500 electrical and optical responses recorded from a crayfish walking leg nerve.

In this experiment, the top surface of the nerve was positioned 30-40 micrometers below the glass-saline interface. Standard deviations of the noise in the first 2 ms were 44 pm and 38 pm (pm: picometer) for FIG. 3A and FIG. 3B, respectively. Because the path length signal ($\Delta p$) was extracted from constant amplitude fringes, the noise levels in the graphs were expected to be constant before and after the stimulation. Upward and downward features of the optical signal indicated swelling and shrinkage directions, respectively. Interestingly, PS-OLCR signals recorded from close (<1 mm) but spatially distinct sites on the same nerve showed optical path length change due to swelling (FIG. 3A) and shrinkage (FIG. 3B) with a magnitude of approximately 0.5 nm. The optical path length change (~0.5 nm) divided by the refractive index of the saline solution (~1.325) gave a magnitude of the transient surface displacement (~0.38 nm).

Electrical current stimulation pulses (300 µA, 50 µs) were presented at 2 ms in the records and resulted in an artifact in the recorded electrical, signal preceding the compound action potential. Because electrical signals were recorded differentially using a pair of platinum electrodes placed in the nerve chamber (FIG. 2), the action potential is thought to have arrived at the first and second recording electrodes at the negative and positive peaks of the electrical signal, respectively. Consequently, zero-crossing of the electrical signal indicated time of arrival of the compound action potential at the optical measurement site positioned between the recording electrodes. Because surface displacements measured by PS-OLCR were nearly coincident with the zero-crossing of action potential records, optical signals were believed to originate from neural activity. Moreover, time duration and amplitude of the optical signal were similar to values reported previously.

Figure 4:
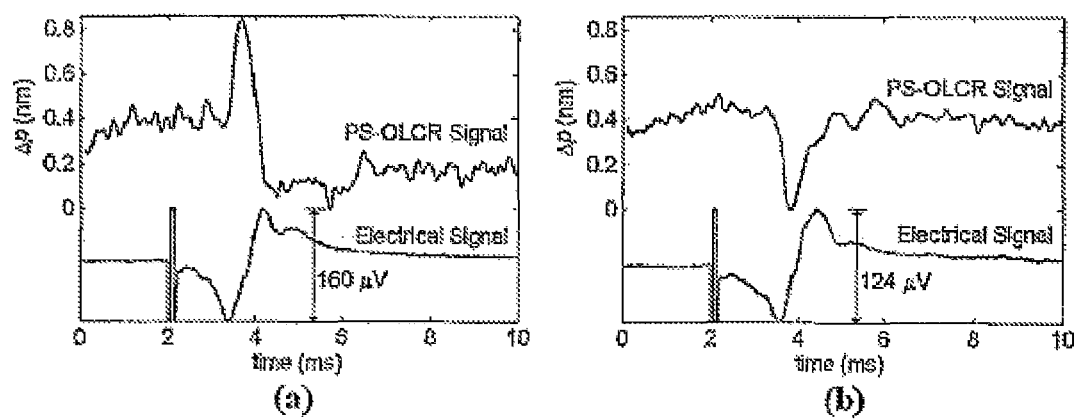
FIG. 4 illustrates the optical, path length change due to surface displacement of a stimulated crayfish leg nerve. Stimulus (300 µA, 50 µs) is at 2 ms. (a) and (b) are recorded from spatially close (<1 mm), but different points on the nerve. 500 responses are averaged in each trace.

The experiment was repeated using a second crayfish walking leg nerve. Separation between top surface of the nerve and glass-saline interface was 280 µm. Electrical current stimulation pulses (300 µA, 50 µs) were presented at 2 ms in the records. FIG. 4A shows the average of 250 responses recorded from the top surface of the nerve. Standard deviation of the noise in the first 2 ms of the optical signal was 39 pm, When the action potential reached the optical measurement site (approximately zero-crossing of the averaged action potential, trace), corresponding changes in optical path length occurred. The sharp peak is PS-OLCR signal represents 1.1 nm optical path length change due to 0.83 nm swelling of the nerve surface. Following the sharp peak, FIG. 4A contains a feature between 8-12 ms. Because the delayed feature occurs after the action potential record, its origin is unclear.

Without changing lateral position of the specimen, depth resolved features were first identified in an A-scan, and a surface 15 µm below the overlying saline-neural interface (295 µm below the glass-saline interface) was probed (FIG. 4B). An average of 250 responses resulted in a standard deviation of 114 pm in the first 2 ms. The increase in the noise level could be due to reduction in signal to noise while probing inside the nerve. Although a feature was observed around 4.5 ms, which were reversed compared to the peak in FIG. 4A, this signals may be different because it originates from inside the nerve.

Using a third crayfish leg nerve, a control experiment was performed with top surface of the nerve positioned 75 µm below the reference glass-saline interface. Results with stimulus amplitude below and above the activation threshold are presented in FIG. 5. Stimuli with 50 µs duration were presented at 2 ms in all records, and associated stimulus artifacts were visible in the electrical signals. Each trace in FIG. 5 is the average of 100 responses.

Figure 5:
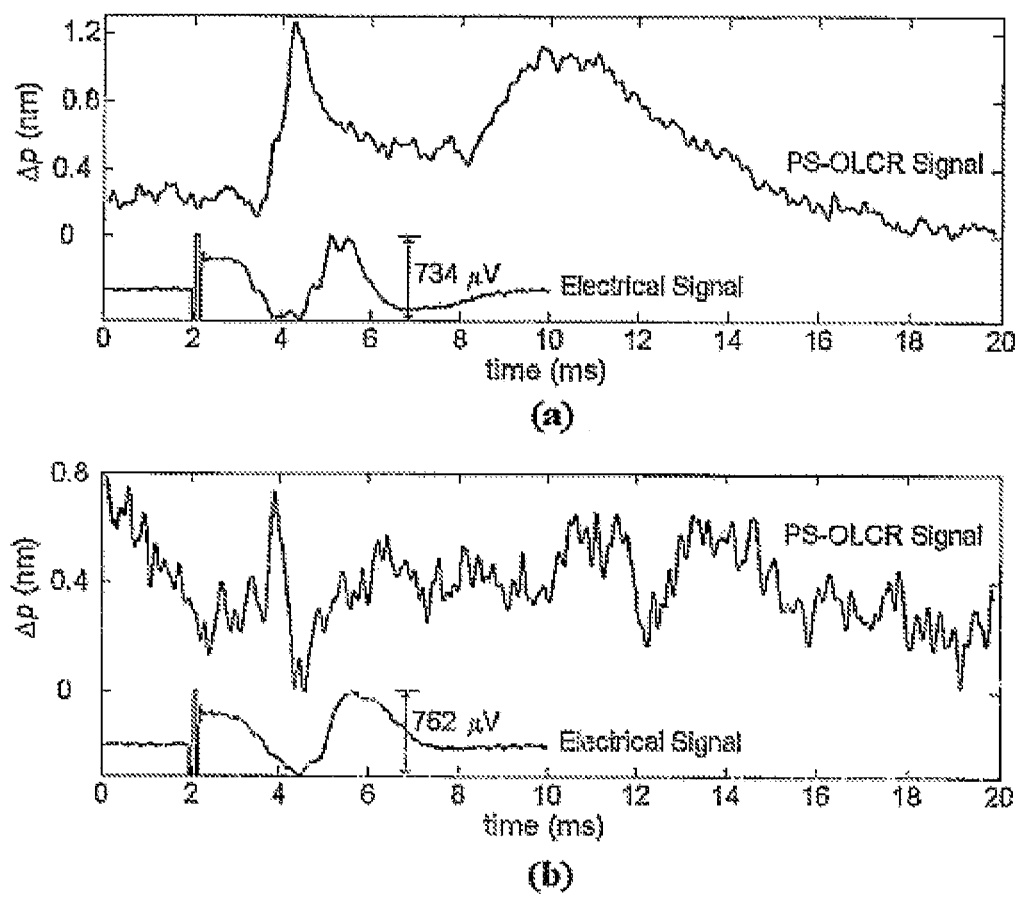
FIG. 5 illustrates the optical path length, change due to surface displacement of a stimulated crayfish leg nerve. Stimulus (300 µA, 50 µs) is at 2 ms. (a) and (b) are recorded from top surface and 15 µm below the top surface, respectively. 250 responses are averaged in each trace.

With the current amplitude of 60 µA for stimulation pulses, an electrical action potential was not produced and no sign of transient surface displacement was observed in the optical records FIGS. 5A and 5C). When current amplitude of stimulation pulses was increased to 100 µA, electrical, optical records show evidence of neural activity (FIGS. 5B and 5D). Measured signals indicated optical path Length change due to transient shrinkage on the order of 1 nm, which corresponds to physical displacement of 0.75 nm. Standard deviations of optical path length change recorded by PS-OLCR in the first 2 ms were 96 pm (FIG. 5A), 117 pm (FIG. 5B), 159 pm (FIG. 5C), and 110 pm (FIG. 5D). This experiment was repeated several times with stimulus amplitudes below (60 µA) and above (100 µA) the activation threshold each time the outcome was similar to the results presented in FIG. 5.

Moreover, when the physiological threshold for action potential stimulation was considerably increased after 2 hours, the control experiment was resumed. Stimulation pulses with current amplitude of 1.4 mA did not produce electrical or optical signals. Increasing the stimulation amplitude to 3 mA resulted in both electrical action potential and optical signal due to surface displacement similar to the results presented in FIG. 5. Based on the results of control experiments, it appears that the measured transient surface displacements were due to propagating action potentials and do not represent a stimulation artifact.

Example 4

Comparison of the Electrical and Optical Signals

Electrical current pulses are able to stimulate action potential propagation using intra-cellular or extra-cellular electrodes. Similar electrodes can record voltage difference due to action potential propagation. Because as use of such electrodes in many clinical applications is infeasible and undesirable in view of potential irreversible damage to nerve fibers, a noninvasive technique for measuring neural activity is useful. Optical differential phase measurements recorded by PS-OLCR can detect neural activity associated with action potential propagation.

Figure 6:
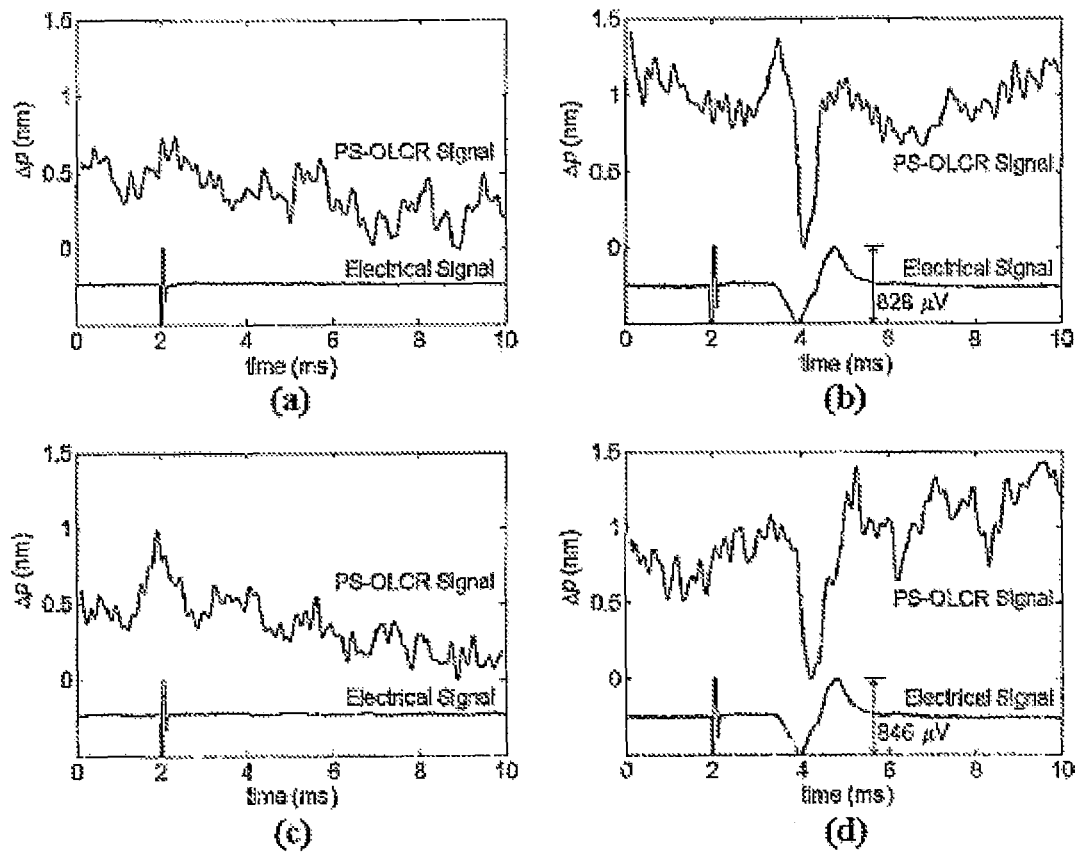
FIG. 6 illustrates a control experiment of surface displacement with stimulus amplitude below and above the action potential threshold. Stimulus duration is 50 µs and presented at 2 ms. (a) and (c) with stimulus amplitude of 60 PA, and (b) and (d) with stimulus amplitude of 100 µA. 100 responses are averaged in each trace.
Figure 7:
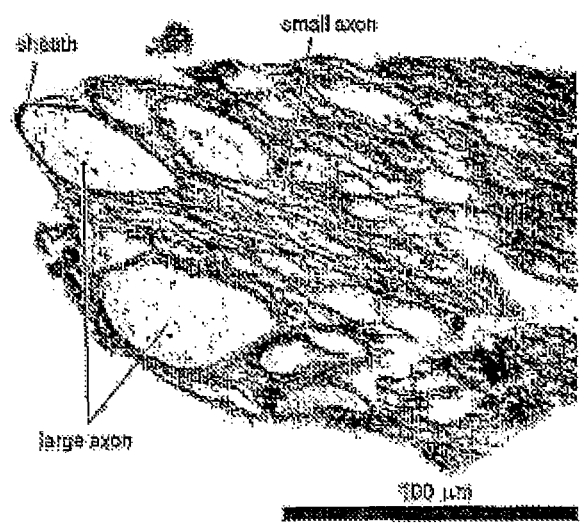
FIG. 7 illustrates the histology (trichrome staining) of a crayfish walking leg nerve.

Because electrical and optical signals are distinct manifestations of neural activity, comparison of these signals requires analysis. The electrical signal is a compound action potential produced by many axons (~1-50 µm in diameter), while the PS-OLCR signal—due to a small diameter beam spot (4 µm) on the nerve—originates from one or a few closely spaced axons. A cross-sectional histological view of a crayfish nerve using a trichrome stain (FIG. 6) illustrates the closely spaced packing of axons. Despite these distinctions, the electrical signal is used to predict action potential arrival time at the optical recording site. A single axon (e.g. squid giant axon) may represent the best model to compare and interpret timing of electrical and optical signals.

Therefore, the present invention is well adapted to attain the ends and advantages mentioned as well as those that are inherent therein. While numerous changes may be made by those skilled in the art, such changes are encompassed within the spirit of this invention as defined by the appended claims.

What is claimed is:

1. A device for detecting neural activity beam comprising:
a. a beam combiner configured to combine light;
b. a broadband source optically linked to the beam combiner;
c. an aiming beam source optically linked to the beam combiner;
d. a separator linked to the beam combiner and configured to separate light into a reference beam and a sample beam; reference optics linked separator, wherein the reference optics includes a phase modulator coupled to a rapid scanning delay line; sample optics operably linked to the separator;
e. a recombiner optically linked to the reference optics and sample optics configured to combine light;

f. an optical spectrometer optically connected to the recombines and configured to detect a plurality of spectral interference densities from the recombiner; and g. a processor processes detected spectral interference densities to produce transient surface displacement information of a neuron, wherein the processor transforms the detection of the transient surface displacement information into an indicator of neural activity in the neuron.

2. The device of claim 1, further comprising a neural stimulator.

3. The device of claim 2, wherein the neural stimulator is selected from the group consisting of an optical stimulator, an electrical stimulator, a chemical stimulator, and combinations thereof.

4. The device of claim 1, wherein the system has a surface displacement sensitivity of 0.1 nanometers.

5. The device of claim 1, wherein the system has a surface displacement temporal resolution of 0.1 microseconds.

6. The device of claim 1, wherein the transient surface displacement information includes a $\Delta p$ that is calculated from a differential phase ($\Delta\phi$) sensitivity of the detected spectral interference densities and a center wavelength of the broadband source ($\lambda o$) using the equation: $\Delta p = (\lambda o/4\pi)\Delta\phi$.

7. The device of claim 1, wherein the transient surface displacement information includes a displacement of one or more neural cell surfaces.

8. The device of claim 1, wherein the processor transforms the detection of inappropriate neural activity into an indicator of a neuropathy in the neuron.

9. The device of claim 1, wherein the processor measures a transient retardation change ($\Delta R$) by a measured intensity changes ($\Delta I$) during an action potential propagation due to the transient retardation change using the equation: $\Delta R = \frac{1}{2} R (\Delta I/I)$, where R is a retardation due to a resting birefringence and I is a resting intensity of light.

10. The device of claim 1, wherein the processor measures changes in a form-birefringence by the transient surface displacement information in response to a rapid repetitive stimuli.

11. The device of claim 1, wherein the rapid scanning delay line comprises a collimator coupled to a diffraction grating, and a lens coupled to the diffraction grating and a mirror on a galvanometer; wherein a separation between the diffraction grating and the lens is adjusted by the rapid scanning delay line to reduce a width of a coherence function to a minimum value.

12. The device of claim 1, wherein the sample optics further comprises at least two birefringent wedges positioned in the sample beam to match a reference path delay of light reflected from the sample beam.

13. The device of claim 1, wherein the phase modulator is driven with a ramp waveform with a voltage amplitude ($V_\pi$) that gives sinusoidal fringe signals at a single carrier frequency.

* * * * *

UNITED STATES PATENT AND TRADEMARK OFFICE
CERTIFICATE OF CORRECTION

PATENT NO. : 9,326,719 B2  
APPLICATION NO. : 13/720563  
DATED : May 3, 2016  
INVENTOR(S) : Taner Akkin et al.

Page 1 of 1

It is certified that error appears in the above-identified patent and that said Letters Patent is hereby corrected as shown below:

In the specification

Column 1, lines 19-21 should read

STATEMENT OF GOVERNMENT SUPPORT

This invention was made with government support under Grant No. EY012877 awarded by the National Institutes of Health. The government has certain rights in the invention.

Signed and Sealed this
Twenty-eighth Day of June, 2016

Michelle K. Lee
*Director of the United States Patent and Trademark Office*